United States Patent
Atwell et al.

(10) Patent No.: US 6,657,189 B2
(45) Date of Patent: Dec. 2, 2003

(54) MAINTAINING MEASUREMENT ACCURACY IN PROMPT GAMMA NEUTRON ACTIVATION ANALYZERS WITH VARIABLE MATERIAL FLOW RATES OR MATERIAL BED DEPTH

(75) Inventors: Thomas L. Atwell, Escondido, CA (US); Victor W. Lanz, Carlsbad, CA (US); Anton M. Lucchin, San Diego, CA (US)

(73) Assignee: Analyser Systems AG, Zug (CH)

( * ) Notice: Subject to any disclaimer, the term of this patent is extended or adjusted under 35 U.S.C. 154(b) by 67 days.

(21) Appl. No.: 10/098,884

(22) Filed: Mar. 15, 2002

(65) Prior Publication Data

US 2003/0102428 A1 Jun. 5, 2003

Related U.S. Application Data

(63) Continuation-in-part of application No. 10/011,048, filed on Nov. 7, 2001.

(51) Int. Cl.⁷ .............................................. G01N 23/222
(52) U.S. Cl. ............................ 250/252.1; 250/368.1; 378/44
(58) Field of Search .......................... 250/252.1, 359.1, 250/358.1, 390.04, 505.1; 378/44, 45, 54, 55; 376/159

(56) References Cited

U.S. PATENT DOCUMENTS

| | | | | | |
|---|---|---|---|---|---|
| 4,024,393 | A | * | 5/1977 | Braun et al. | 376/159 |
| 4,582,992 | A | * | 4/1986 | Atwell et al. | 250/359.1 |
| 4,694,165 | A | * | 9/1987 | Proctor et al. | 250/252.1 |
| 4,882,927 | A | * | 11/1989 | Gould | 73/1.01 |
| 5,241,569 | A | * | 8/1993 | Fleming | 376/159 |
| 5,330,621 | A | * | 7/1994 | Visuri et al. | 162/49 |
| 5,748,509 | A | * | 5/1998 | Fewster | 703/6 |
| 6,130,931 | A | * | 10/2000 | Laurila et al. | 378/45 |
| 6,157,034 | A | * | 12/2000 | Griebel et al. | 250/358.1 |

* cited by examiner

*Primary Examiner*—Constantine Hannaher
*Assistant Examiner*—Otilia Gabor
(74) *Attorney, Agent, or Firm*—Higgs, Fletcheer & Mack LLP; Charles F. Reidelbach, Jr.

(57) ABSTRACT

A method of maintaining measurement accuracy of specific constituents in prompt gamma neutron activation analyzers in a flow of bulk material having a known range of flow rates. The method comprises the steps of providing a plurality of samples of the bulk material for insertion into the analyzer in geometries and quantities referred to as loading profiles. Each of the loading profiles is inserted into the analyzer and measured long enough to yield a measurement uncertainty that is small compared to the observed differences in analysis results from one loading to another. The results are recorded and differences computed as measured errors for subsequent mathematical generation of the expected error at any loading value.

16 Claims, 11 Drawing Sheets

20 kg/m Loading Profile

Layer #1    2 wide x 5 long    = 10 Units  (Lowermost Layer)
            Total Units        = 10 Units 20 kg/m Loading Profile Layer #1    2 wide x 5 long   = <u>10 Units</u>  (Lowermost Layer)
    Total Units                      = 10 Units 40 kg/m Loading Profile

| | | |
|---|---|---|
| Layer #2 | 2 wide x 5 long | = 10 Units  (Uppermost Layer) |
| Layer #1 | 2 wide x 5 long | = 10 Units  (Lowermost Layer) |
| | Total Units | = 20 Units |

70 kg/m Loading Profile

| | | |
|---|---|---|
| Layer #3 | 3 wide x 5 long | = 15 Units (Uppermost Layer) |
| Layer #2 | 2 wide x 5 long | = 10 Units |
| Layer #1 | 2 wide x 5 long | = 10 Units (Lowermost Layer) |
| | Total Units | = 35 Units |

90 Kg/m Loading Profile

| Layer #4 | 2 wide x 5 long | => 10 Units (Uppermost layer) |
| Layer #3 | 3 wide x 5 long | => 15 Units |
| Layer #2 | 2 wide x 5 long | => 10 Units |
| Layer #1 | 2 wide x 5 long | => 10 Units (Lowermost layer) |
| | Total Units | = 45 Units |

100 Kg/m Loading Pattern

| Layer #4 | 3 wide x 5 long | = 15 Units | (Uppermost Layer) |
| Layer #3 | 3 wide x 5 long | = 15 Units | |
| Layer #2 | 2 wide x 5 long | = 10 Units | |
| Layer #1 | 2 wide x 5 long | = 10 Units | (Lowermost layer) |
| | Total Units | = 50 Units | |

110 Kg/m Loading Pattern

| Layer #5 | 1 wide x 5 long | = 5 Units | (Uppermost layer) |
| Layer #4 | 3 wide x 5 long | = 15 Units | |
| Layer #3 | 3 wide x 5 long | = 15 Units | |
| Layer #2 | 2 wide x 5 long | = 10 Units | |
| Layer #1 | 2 wide x 5 long | = 10 Units | (Lowermost layer) |
| | Total Units | = 55 Units | |

130 Kg/m Loading Pattern

| Layer #5 | 3 wide x 5 long | = 15 Units | (Uppermost layer) |
| Layer #4 | 3 wide x 5 long | = 15 Units | |
| Layer #3 | 3 wide x 5 long | = 15 Units | |
| Layer #2 | 2 wide x 5 long | = 10 Units | |
| Layer #1 | 2 wide x 5 long | = 10 Units | (Lowermost layer) |
| | Total Units | = 65 Units | |

160 Kg/m Loading Pattern

| | | | |
|---|---|---|---|
| Layer #6 | 3 wide x 5 long | = 15 Units | (Uppermost layer) |
| Layer #5 | 3 wide x 5 long | = 15 Units | |
| Layer #4 | 3 wide x 5 long | = 15 Units | |
| Layer #3 | 3 wide x 5 long | = 15 Units | |
| Layer #2 | 2 wide x 5 long | = 10 Units | |
| Layer #1 | 2 wide x 5 long | = 10 Units | (Lowermost layer) |
| | Total Units | = 80 Units | |

180 Kg/m Loading Pattern

| Layer #7 | 2 wide x 5 long | = 10 Units | (Uppermost layer) |
| Layer #6 | 3 wide x 5 long | = 15 Units | |
| Layer #5 | 3 wide x 5 long | = 15 Units | |
| Layer #4 | 3 wide x 5 long | = 15 Units | |
| Layer #3 | 3 wide x 5 long | = 15 Units | |
| Layer #2 | 2 wide x 5 long | = 10 Units | |
| Layer #1 | 2 wide x 5 long | = 10 Units | (Lowermost layer) |
| | Total Units | = 90 Units | |

View of layers #1, 2, & 7 on the belt

View of layers #3 4, 5, & 6 on the belt

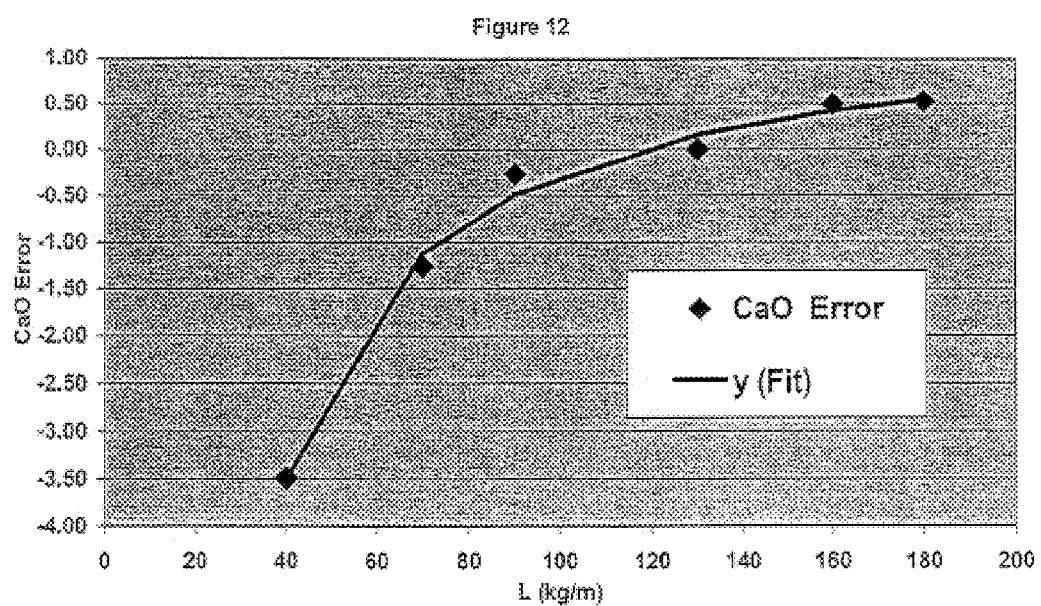

MAINTAINING MEASUREMENT ACCURACY IN PROMPT GAMMA NEUTRON ACTIVATION ANALYZERS WITH VARIABLE MATERIAL FLOW RATES OR MATERIAL BED DEPTH

RELATION TO OTHER PATENT APPLICATIONS

This is a continuation-in-part application of my previously filed United States patent application Maintaining Measurement Accuracy in Prompt Gamma Neutron Activation Analyzers with Variable Material Flow Rates or Material Bed Depth filed Nov. 7, 2001 and given Ser. No. 10/011,048.

BACKGROUND OF THE INVENTION

1. Field of the Invention

This invention relates to the field of bulk material handling. More precisely, it relates to devices employing nuclear radiation to measure amounts of specific constituents in bulk materials in a continuous process.

2. Description of the Prior Art

A Prompt Gamma Neutron Activation Analyzer, or PGNAA device bombards bulk amounts of material, such as limestone, coal, sand, mineral ores, wheat and the like with neutrons causing specific constituents in these materials to respond by issuing gamma rays that are subsequently measured to indicate concentrations of these constituents. Constituents such as calcium oxide (CaO) in limestone, sulfur (S) in coal, moisture ($H_2O$) in sand, iron (Fe) in mineral ores, and proteins containing nitrogen (N) in wheat, are determined by using such a PGNAA. The bulk materials are delivered to the PGNAA on a rubber conveyor belt and passed through a radiation chamber where the materials are exposed to the neutron radiation. The gamma radiation caused thereby is registered on instruments that provide a direct readout of these constituents. Such a real-time analysis is needed in order to insure accurate tracking of concentrations of these constituents to provide a basis for delivering bulk materials carrying an accurate amount of whatever constituent is desired.

Depending on the type of process or application, the flow rate or mass loading of material to be measured in the PGNAA is not constant, resulting in variable material loads per unit length inside the radiation chamber. Variations of material loading can be continuous and can extend from empty to full PGNAA capacity.

The typical practice in the prior art of setting up and calibrating a PGNAA is to load the conveyor belt with a sample of the bulk material, in the particle size distribution and average tonnage rate (translated into the mass loading per unit length of the bed of material on the conveyor belt) expected in operation, where the amount of the constituent to be measured is accurately known. This "standard" bulk material is usually mixed extremely well and many samples of the mix are taken and evaluated by chemical and other means to determine the exact concentration of the specific constituent. A large quantity of this mix, in sufficient size to emulate a real-time pass-through of the bulk material, is then tested under the PGNAA and the measurement instruments adjusted to indicate the amount of constituent that is already known in the "standard" material.

This "standard" material is expensive to make, difficult to keep isolated, costly to store, and the numerous tests run on it are expensive and time-consuming. In addition, constant tonnage flow rate through the PGNAA (constant mass loading per unit length) is difficult if not impossible, to achieve and maintain and surges in product create changes in tonnage and flow rates. It has been shown that these departures from desired optimum flow rate causes deterioration in the accuracy of the measurements. This leads to sales or quality of bulk material too rich or too lean in one or major specific constituents.

If the PGNAA is calibrated with a "standard" of a given material mass loading, it will measure elemental composition accurately only when analyzing that same material mass loading. The PGNAA will produce significant measurement errors when analyzing materials of a different mass from that used in calibration. In general, PGNAA devices produce larger measurement errors when the mass loading is lower, and smaller errors when the mass loading is higher than the mass loading contained in the "standard" during the calibration. The technical reasons for the PNGAA measurement errors at non-calibrated tonnage or mass loadings are described below. The consequence of this phenomenon is that analysis measurements of variable material streams are not accurate and not reliable enough for process control.

The amount of material flow is measured by a conventional weigh scale or flow meter and reported continuously and instantaneous as F in units of tons per hour (TPH). Given the conveyor belt speed B in units of meters per second (m/s), the instantaneous material loading L in mass units of kilograms per meter (kg/m) can be determined by:

$$L = F/(3.6 \times B) \qquad \text{Equation I.}$$

Using Equation 1, if the belt speed B=1.95 m/s and the F=400, 800, and 1200 TPH, then loadings L=56.98, 113.96 and 170.94 kg/m respectively. Conversely, the tonnage flow rate through the PGNAA can be calculated by:

$$F = 3.6 \times B \times L \qquad \text{Equation 2.}$$

The technical reasons for the PNGAA measurement errors at non-calibrated tonnage or mass loadings are caused by non-constant amounts of constituent signal emanating: (1) from: the conveyor belt, and (2) from the walls, irradiating, shielding, detectors and construction materials used inside the PGNAA device itself. Constituent signals emanating from any source other than the bulk material to be measured are referred to as "background signal".

Conveyor belts used in the coal, cement, and mineral ore industries are one source of constituent PGNAA background. These belts are primarily Styrene Butadiene Rubber (SBR), in approximately a 1:4 blend of Styrene and Butadiene respectively. Styrene is $C_8H_8$ and Butadiene is $C_4H_6$. Additives to the SBR rubber include ~0.5% sulfur for vulcanization, nylon or polyester cords for reinforcement, 10–30% oil and 10–15% $CaCO_3$ for flexibility, and a few percent $SiO_2$ and $Al_2O_3$ for improved wear resistance.

The materials of the conveyor belt and the walls and internals of PGNAA itself, referred to as "background materials", will capture neutrons and emit gamma rays and produce PGNAA signal just as the bulk material itself, producing constituent background signals. Compounding this problem, the portion of the gamma ray spectra captured by the detectors that is attributable to the background materials, is not a constant signal because the amount of bulk material inside the measurement zone influences the magnitude of neutron flux impinging on the background materials. Therefore, the errors associated with the unknown magnitude of background signal from the constituents such as H, C, S, N, Ca, Al, Si, and others in the background materials prevent a prior art PGNAA device from accurately reporting only the analysis of the constituents in the bulk material itself. Furthermore, variable amounts of both neutron and gamma ray attenuation caused by variations in the thickness of the bulk material bed also contribute to PGNAA errors because the relative magnitudes of the constituent signals emanating from the bulk material itself are not constant with variable belt loading. In summary the measurement errors are a function of a multitude of parameters, each in some way caused by and related to variations in tonnage or flow rate. For these reasons, the prior art method of simply subtracting constant values of background from each measured constituent will not achieve measurement accuracy in PGNA analyzer applications operating under variable material flow conditions.

In prior applications of PGNA analyzers, considerable cost and effort has been applied in the industry to achieve near-constant flow rate and mass thickness. Such means have included the use of surge hoppers and constant flow feeders, variable speed conveyor belt drives, and vertical, plug-flow type PGNA analyzers, all so as to deliver a constant mass of bulk material (kg/m) or material cross-section to the measurement region.

In prior art, a PGNA analyzer is conventionally calibrated using a set of two or more unique and well-known mixtures of (1) high-purity base materials the amounts of which are carefully weighed prior to mixing, or (2) well-homogenized mixtures of representative unknowns that have been blended, sampled and analyzed for element or compound analysis by conventional laboratory means. In either case the chemistry of each standard is known quite accurately and allow the set of standards to be utilized as a general calibration of the PGNA apparatus. In prior art each standard in the set contains the same fixed mass and length. The entire mass of the standard fills the analyzing volume, and is either contained in a single structural unit, or bound together as a single unit by cement or epoxy block.

The length of the standards is determined by (1) the length of the analyzing volume or (2) a length which if longer, would yield no additional analysis signal. The mass of standard material in each set is configured to match the average material loading (kg/m) the PGNA analyzer will measure in the application. These single mass standards are designed for insertion into the analyzer for the purpose of calibrating the analyzer over the number and range to elemental compositions expected to pass through the analyzer over the course of its service.

Testing and calibration of analyzers using prior art standards can only be done at one fixed flow rate (TPH) or mass loading (kg/m). This is a serious limitation to properly calibrate an analyzer over a range of flow rates, when such PGNA analyzing apparatus is inherently sensitive to amount of material it is measuring due to unknown contributions of background terms.

SUMMARY OF THE INVENTION

This invention is directed towards PGNAA devices analyzing variable loads. The invention describes a method of quantifying the analytical measurement error resulting from material mass loadings different from the loading at which the analyzer was calibrated, and a method of compensation for this error, also referred to as "analysis bias", in order to produce accurate analysis results under all load conditions.

The inventive process described herein provides for measurement compensation of on-line Prompt Gamma Neutron Activation Analysis (PGNAA) equipment under conditions of variable flow rate or material mass loading. The process includes utilization of (1) one or more sets of calibration materials in the form of standard geometric units that can be arranged to represent the variations in flow rate and mass loading as well as material geometric profile, (2) a method to quantify the measurement errors of each constituent analyzed over a range of material loadings, and (3) a method to predict by calculation the amount of expected error for each constituent at any given flow rate or loading, and (4) a method to calculated and remove the expected errors for each constituent measured by utilizing the real-time flow rate or tons per hour signal, together with the mathematical functions and parameters derived in points (1) to (3). This process greatly improves PGNA analyzer measurement accuracy and is particularly well suited for industrial applications. The process can be utilized on new or existing PGNAA equipment.

DESCRIPTION OF THE PREFERRED EMBODIMENT

Figure 1A:
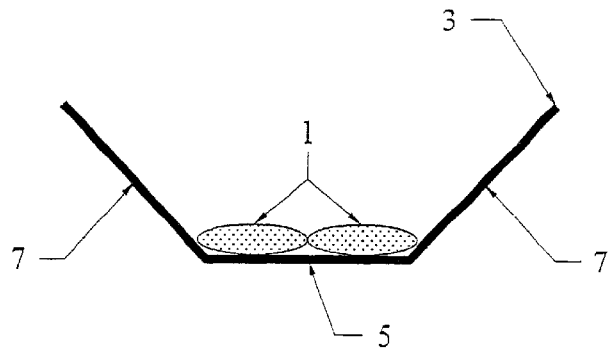
FIG. 1a is an illustrative end view of a trough-type conveyor belt, taken along lines 1A—1A in FIG. 1B showing the packages of unit standards loaded therein in a loading profile of 20 kg/m.
Figure 1B:
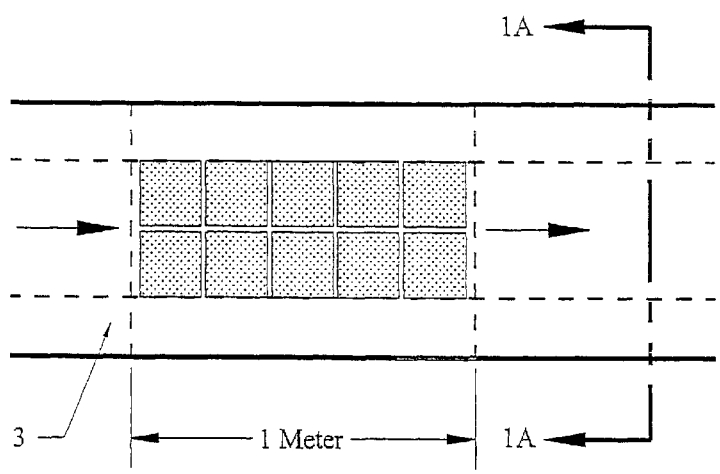
FIG. 1B is an illustrated top view of the conveyor belt shown in FIG. 1A showing how the packages of unit standards are arranged.

As shown in FIGS. 1A and 1B through 9A and 9N, the first step in this inventive process is to provide a set of uniformly loaded packages or containers 1 filled with well-homogenized and characterized material or mixture of materials. Packages 1 are loaded in different profiles in a trough-type conveyor belt 3 as shown in FIGS. 1A and 1B through 9A and 9B. As shown in FIG. 1A, belt 3 comprises a base 5 and a pair of opposed, upwardly slanted sidewalls 7. The set of packages is commonly referred to as a "standard". These standards differ from those used in prior art, in that each standard package 1 is of a size and shape for ready handling by an individual and able to be stacked in a variety of geometries. Each unit package 1 contains precisely the same constituent chemistry as the entire standard set.

The size of the unit standards is dimensioned such that the units can be easily stacked and configured to approximately duplicate actual conditions of materials to be analyzed. It is important that the number and sizes of the unit standards be designed to allow a stacking pattern that will approximate actual mass and profiles of real materials. Examples of stacks of packages 1 that approximate actual mass and profile of real materials under PGNAA operating conditions are shown in FIGS. 1–9. The number of packages used in length should equal the number required to span the length of the PGNAA irradiation chamber or analyzing region. In the examples shown, the analyzing region is five packages long. Likewise, the number of packages in width at a given vertical level should equal the width of the bulk material at that such vertical level. In the examples, the width of the packages varies from two to three units wide to represent the loading patterns experienced on a trough-type conveyor belt. The physical shape of the unit standard is not limited to being square as illustrated. The number is also without limitation. In the extreme, loose bulk material comprising the standard can be used and placed on the conveyor belt in varying loading amounts such as 20, 40, 70, 90, 100, 110, 130, 160, 180 kilograms per meter (kg/m) although considerations of handling, losses and contamination limit practical long-term use.

Figure 2A:
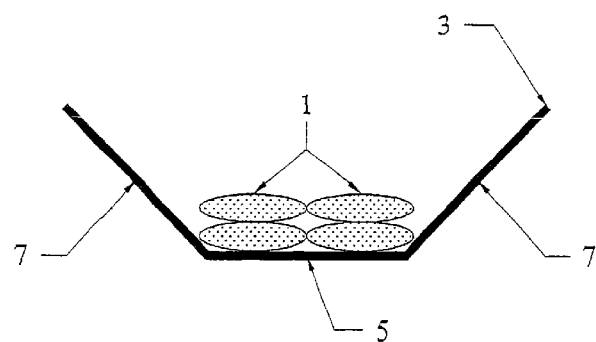
FIG. 2A is an illustrative end view of a trough-type conveyor belt, taken along lines 2A—2A in FIG. 2B showing the packages of unit standards loaded therein in a loading profile of 40 kg/m.
Figure 2B:
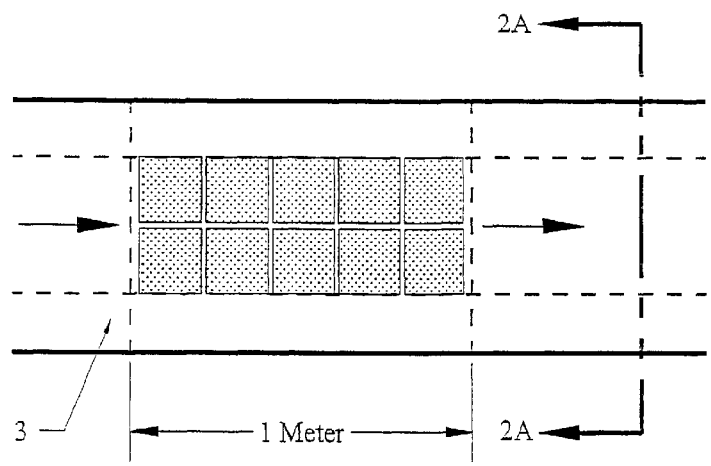
FIG. 2B is an illustrated top view of the conveyor belt shown in FIG. 2A showing how the packages of unit standards are arranged.
Figure 3A:
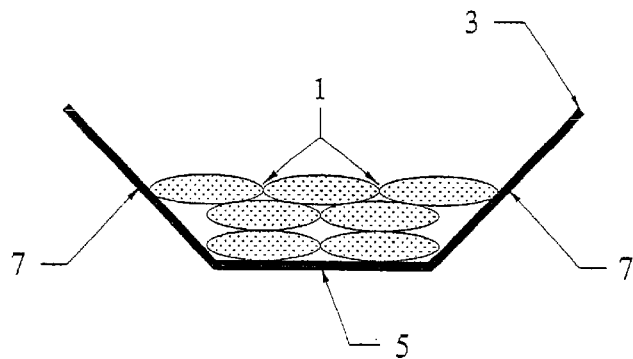
FIG. 3A is an illustrative end view of a trough-type conveyor belt, taken along lines 3A—3A in FIG. 3B showing the packages of unit standards loaded therein in a loading profile of 70 kg/m.
Figure 3B:
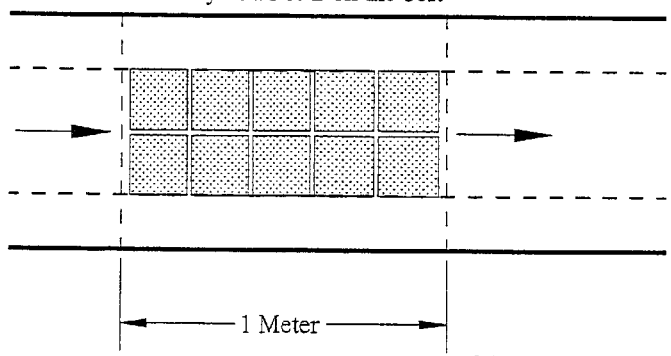
FIG. 3B is an illustrated top view of the conveyor belt shown in FIG. 3A showing how the packages of unit standards are arranged.
Figure 3B:
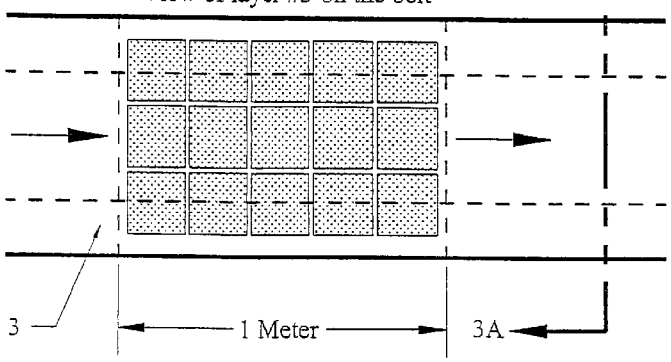
Figure 4A:
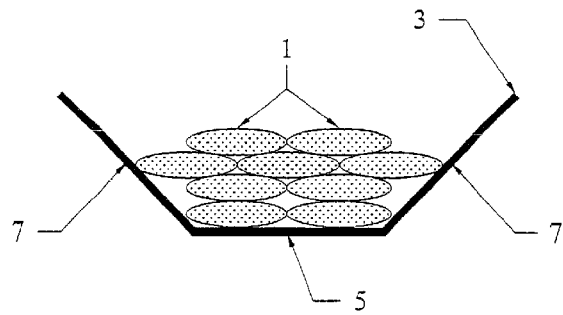
FIG. 4A is an illustrative end view of a trough-type conveyor belt, taken along lines 4A—4A in FIG. 4B showing the packages of unit standards loaded therein in a loading profile of 90 kg/m.
Figure 4B:
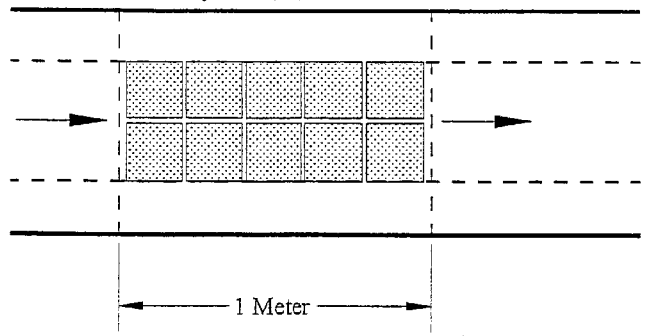
FIG. 4B is an illustrated top view of the conveyor belt shown in FIG. 4A showing how the packages of unit standards are arranged.
Figure 4B:
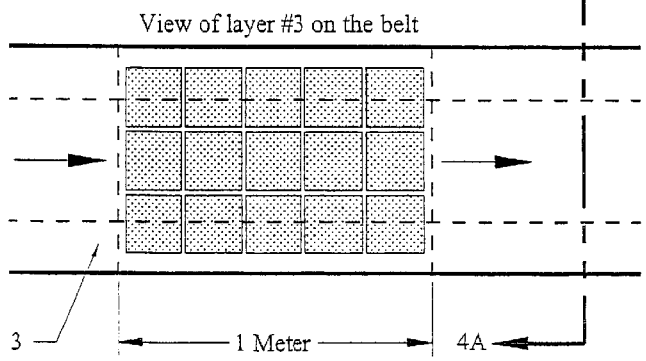
Figure 5A:
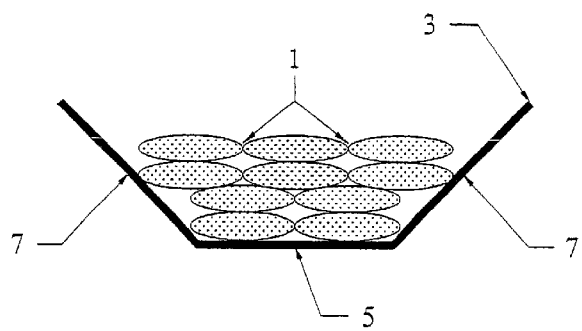
FIG. 5A is an illustrative end view of a trough-type conveyor belt, taken along lines 5A—5A in FIG. 5B showing the packages of unit standards loaded therein in a loading profile of 100 kg/m.
Figure 5B:
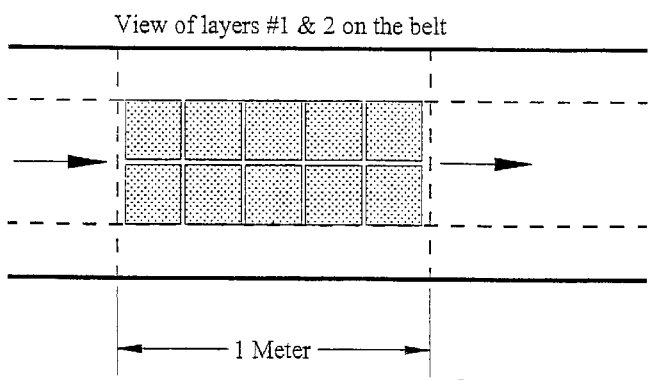
FIG. 5B is an illustrated top view of the conveyor belt shown in FIG. 5A showing how the packages of unit standards are arranged.
Figure 5B:
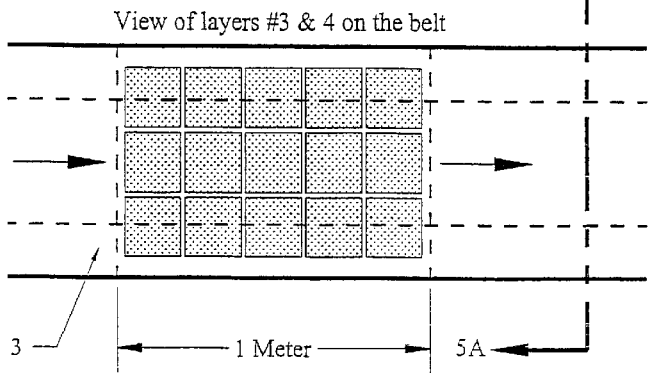
Figure 6A:
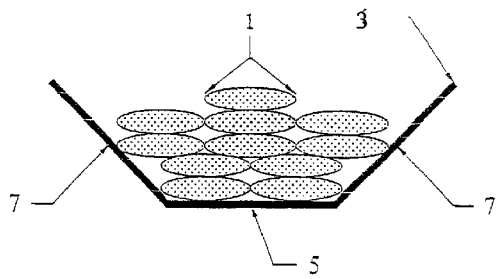
FIG. 6A is an illustrative end view of a trough-type conveyor belt, taken along lines 6A—6A in FIG. 6B showing the packages of unit standards loaded therein in a loading profile of 110 kg/m.
Figure 6B:
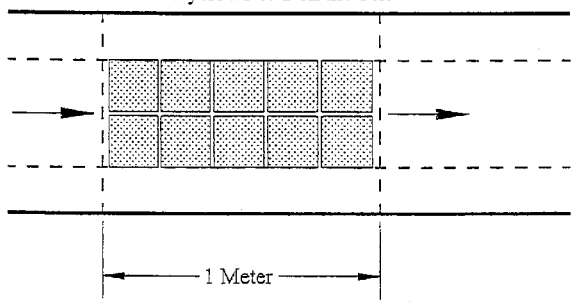
FIG. 6B is an illustrated top view of the conveyor belt shown in FIG. 6A showing how the packages of unit standards are arranged.
Figure 6B:
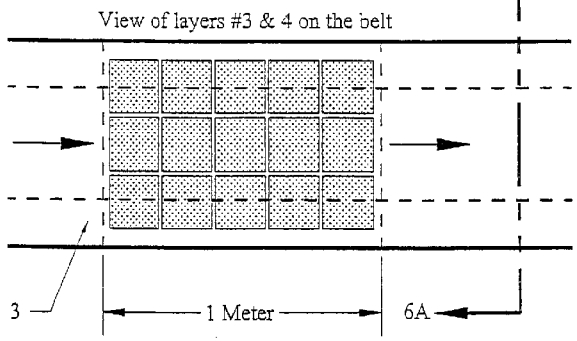
Figure 6B:
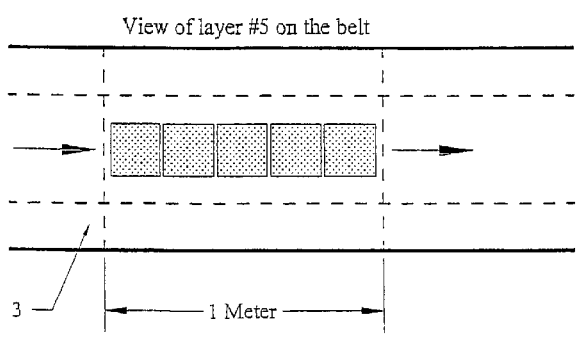
Figure 7A:
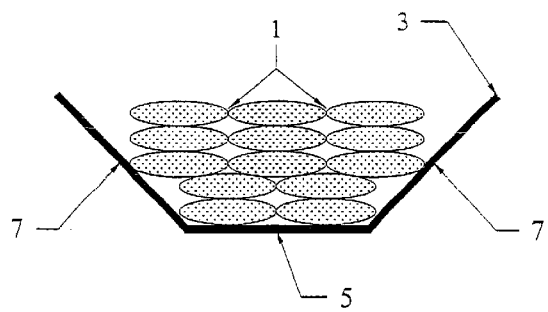
FIG. 7A is an illustrative end view of a trough-type conveyor belt, taken along lines 7A—7A in FIG. 7B showing the packages of unit standards loaded therein in a loading profile of 130 kg/m.
Figure 7B:
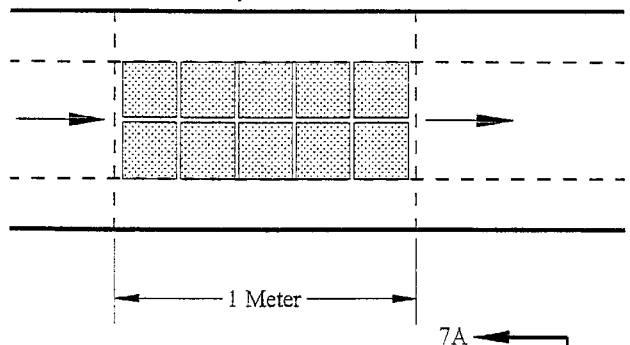
FIG. 7B is an illustrated top view of the conveyor belt shown in FIG. 7B showing how the packages of unit standards are arranged.
Figure 7B:
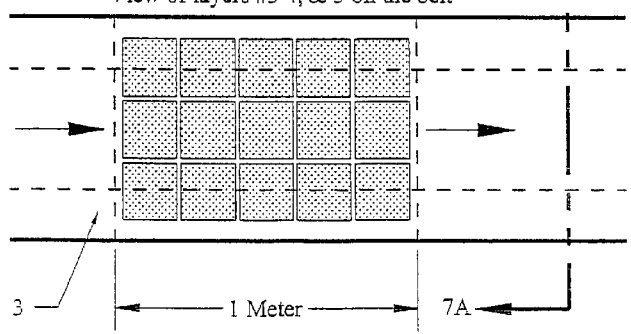
Figure 8A:
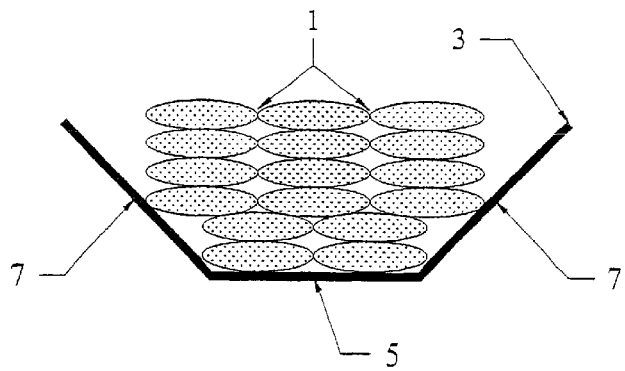
FIG. 8A is an illustrative end view of a trough-type conveyor belt, taken along lines 8A—8A in FIG. 8B showing the packages of unit standards loaded therein in a loading profile of 160 kg/m.
Figure 8B:
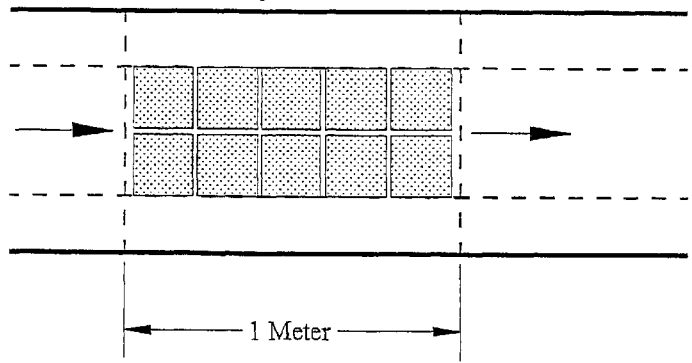
FIG. 8B is an illustrated top view of the conveyor belt shown in FIG. 8A showing how the packages of unit standards are arranged.
Figure 8B:
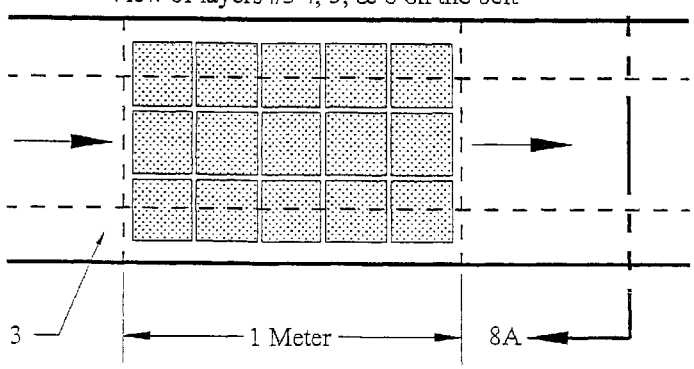
Figure 9A:
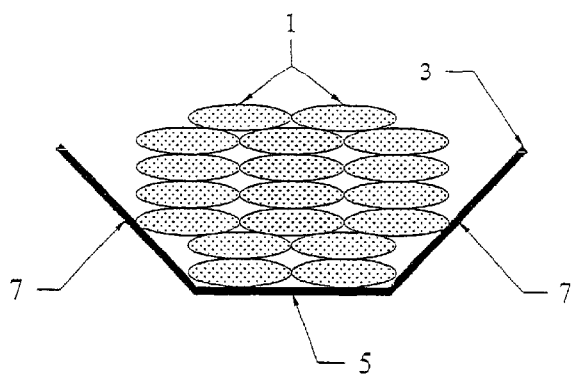
FIG. 9A is an illustrative end view of a trough-type conveyor belt, taken along lines 9A—9A in FIG. 9B showing the packages of unit standards loaded therein in a loading profile of 180 kg/m.
Figure 9B:
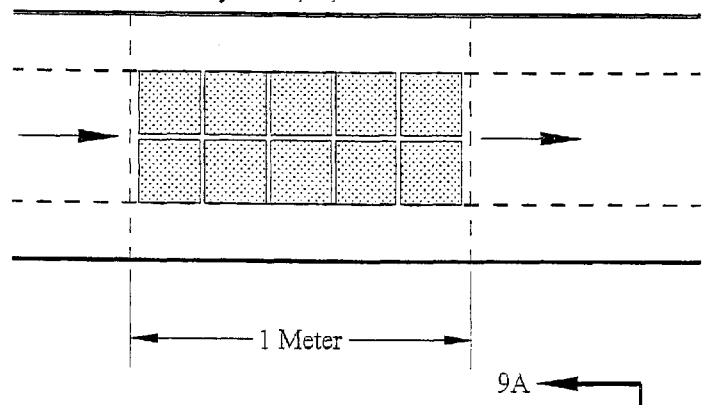
FIG. 9B is an illustrated top view of the conveyor belt shown in FIG. 9A showing how the packages of unit standards are arranged.
Figure 9B:
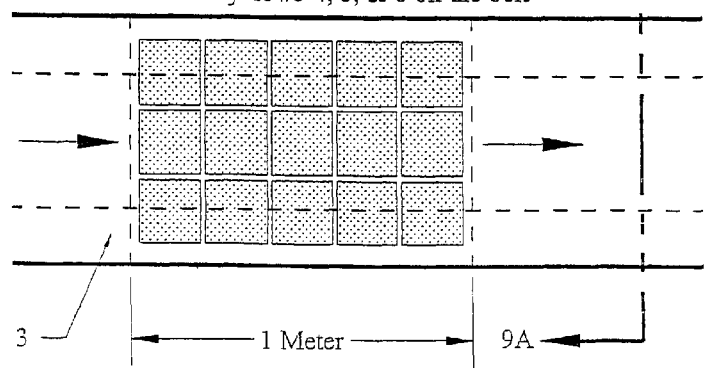
Figure 10:
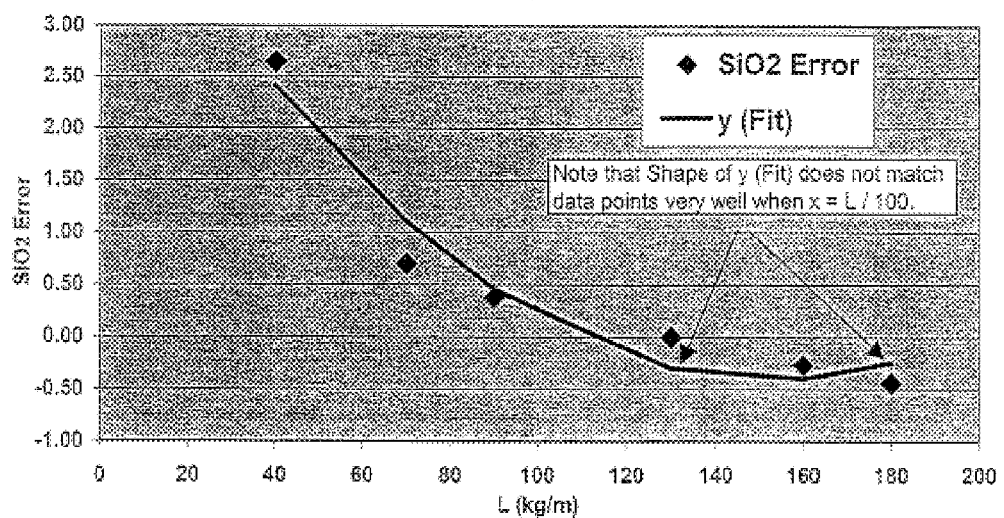
FIG. 10 is a graph of $SiO_2$ error vs. load over a range of 40 to 180 kg/m.

If each package in FIGS. 2A and 2B weigh 2.0 kilograms, and each were 20 cm long, then five units placed end-to-end would span one meter. An array of 20 units would yield a loading of 40 kg/m. If the belt speed B=1.95 meters per second (m/s), then the flow represented would be 291 tons per hour (TPH), see Equation 2 and FIGS. 3A and 3B. The loading patterns are quite flexible and should conform to the physical profile of the material moving through the analyzer at a particular tonnage rate or mass loading.

A further benefit of utilizing small standard units is that a person can perform the loading quite easily without aid of mechanical lifting equipment, at least for units weighing no more than 10 kg. In this example, to achieve a loading of 40 kg over 1 meter, if each unit standard was 1 meter long and weighed 10 kg, stacking four units would achieve the desired profile and load.

The second step of the inventive process is to determine the "errors of the measurements" of one or more of the measured constituents by testing over at least two distinct material loadings of the standard packages and by comparing the measurements of such constituent to its measurement at the reference loading. The following steps give one procedure:

1. Empty the analyzing volume of the analyzer to be tested.
2. Determine the range of tonnage rates over which the PGNAA is to operate by asking the user.
3. Using Equation 1, determine the minimum and maximum loadings spanned by the range over which the analyzer is to operate.
4. Form all of the possible stacking patterns of the unit standards that yield a physical profile similar to actual conditions of real materials, select the two stacking profiles that most closely match the minimum and maximum loadings "L" determined in Step 3, and define them Lmin and Lmax respectively. Use these patterns as the minimum and maximum loadings that will be tested.
5. Select three or more profiles of uniform stacking arrangements that have loadings that are intermediate between Lmin to Lmax, and also yield a physical profile similar to actual conditions of real materials. When completed there will be "n" different loadings. For example, using package loading profiles described in FIGS. 1–9, if Lmin is 40 kg/m and Lmax is 180 kg/m, intermediate values for "L" of 70, 90, 130 and 160 kg/m could be chosen. In this testing scenario "n" equals six.
6. Successively load, measure and remove each of the loading profiles into the PGNAA device.
7. For each loading "L", measure the standard inside the PGNAA for a time long enough to yield a measurement uncertainty that is small compared to the observed differences in results from one loading to another. Analytical results from a PGNAA device follow the laws of random probability and Poisson statistics. Adequate measurement times can be determined experimentally by repeating a given test on the same set and profile of standard packages several times, then comparing the answers on each measured constituent for statistical error. This is referred to, in the PGNAA industry, as measuring the "repeatability". Smaller material loadings will exhibit larger statistical repeatability errors than larger loadings. If the analyzer measures more than one constituent, it is important that all of the constituents measured achieve better statistical repeatability than the amount of measurement error between different material loadings. Repeating Step 6 several times is also useful in evaluating measurement uncertainties by comparing the results of each repetition.

8. Enter the Test number, loading L(i), analysis result for each parameter "j" measured, and the flow rate "F", calculated by Equation 1, into a table. Table 1 is an example showing the results of six different loadings "B" of 40, 70, 100, 130, 160 and 180 kg/m, for measured parameters $SiO_2$ and CaO. The nominal loading in this example was 130 kg/m, a value within the range of "L" for typical tonnage rate (TPH) values.

TABLE 1

| Values Before Compensation (Reference = Test 4) | | | | |
|---|---|---|---|---|
| Test | L kg/m) | F (TPH) | $SiO_2$ | CaO |
| 1 | 40 | 281 | 15.74 | 39.61 |
| 2 | 70 | 491 | 13.79 | 41.84 |
| 3 | 90 | 632 | 13.47 | 42.83 |
| 4* | 130 | 913 | 13.09 | 43.10 |
| 5 | 160 | 1123 | 12.82 | 43.59 |
| 6 | 180 | 1264 | 12.65 | 43.63 |

*Reference Values

For each test, the measurement error relative to the reference loading can now be calculated and tabulated. For each analyzed parameter "j", and at each loading L(i), the error E(j,L(i)) between the measured value M(j,L(i)) and the measured value M(j,Lx) at the "reference" loading Lx (130 kg/m) being is calculated and tabulated. "E" is defined by:

$$E(j,L(i))=M(j,L(i))-M(j,Lx) \text{ for all tests } i \text{ and constituents } j \quad \text{Equation 3.}$$

The results are then tabulated as shown in the example of Table 2, where $SiO_2$ (j=1) and CaO (j=2). Note that the errors for $SiO_2$ and CaO in Test 4 (I=4) are zero, because Test 4 has been chosen as the reference. The reference value would be the result obtained when an analyzer is calibrated at a single reference loading such as Lx. One commonly used measure of the error across all tests is referred to as RMSD, the Root Mean Square Deviation, located at the bottom of the table. The RMSD is 1.15 for the $SiO_2$ values over the loadings tested and 1.55 for the CaO.

RMSD is calculated by computing the square root of the sum of the squares of all the errors divided by the number of errors tests included. After a PGNAA device is compensated for material loading using the methods described herein, the RMSD values become substantially reduced.

TABLE 2

| Error Before Compensation (Reference = Test 4) | | | | |
|---|---|---|---|---|
| Test | L (kg/m) | F (TPH) | $SiO_2$ | CaO |
| 1 | 40 | 281 | 2.65 | −3.49 |
| 2 | 70 | 491 | 0.70 | −1.26 |
| 3 | 90 | 632 | 0.38 | −0.27 |
| 4* | 130 | 913 | 0.00 | 0.00 |
| 5 | 160 | 1123 | −0.27 | 0.49 |
| 6 | 180 | 1264 | −0.44 | 0.53 |
| | | RMSD | 1.15 | 1.55 |

The third step of the inventive process is the prediction of errors of each analyzed constituent, at any given flow rate over the range of flow rates spanned by the tests, given a table of measured errors at discrete flow rates or loadings. The fourth step described below the predicted measurement errors, will be utilized to compensate the PGNAA results. Three examples of general methods used to predict errors at various future loadings having first generated the measured errors over several discrete loadings as described by step two are listed here:

1. Calculation of expected errors by parametric correlation utilizing mathematical functions and parameters determined by "Least-Squares Fitting" or "Linear Regression";
2. Interpolation techniques such as nearest neighbor, linear, cubic, cubic spline and others; and,
3. Rule-based assignment of a previously measured error at a discrete flow rate or loading L that most closely matches the current flow rate or loading.

$$y=a+bx+cx^2+dx^3 \quad \text{Equation 4:}$$

is a conventional method used to mathematically predict the trend of a set of data y correlated to the variable x. The coefficients a, b, c, and d can be determined by least-squares fitting of independent variable y, representing the errors in Table 2, to a variable or function dependent on the amount of loading x in the tests. A linear or $1^{st}$ degree fit contains the first two terms of Equation 4; a quadratic or $2^{nd}$ degree utilizes the first three terms, a cubic or $3^{rd}$ degree fit uses the first four terms and so forth. This invention does not limit the number or the functional form of variable x.

If an analyzer exhibits errors versus belt loading or flow rate, then one of the primary parameters to utilize in predicting the error is a function involving the loading or tonnage rate value itself. Some examples of defining variable x as a function of the loading value L are:
1. x=L (here x is linear with L and has units of kg/m)
2. x=L/100 (here x is linear with L and has units of kg/cm)
3. x=100/L (here x is inversely proportional to L and has units of cm/kg)
4. x=exp(100/L) (here x is an exponential function of L and is dimensionless)
5. x=sin(L) (here x is an sinusoidal function of L and has units of radians)

In addition to utilizing only fitting functions involving the mass loading L, functions of other key parameters can be fit simultaneously, such as moisture, bulk density, asymmetry of loading profile, a constituent exhibiting neutron or gamma ray enhancing or attenuating properties, or a constituent that has a known relationship to the measurement errors associated with non-constant mass loading.

$$y=a+bx+cx^2+du+eu^2+fz+hu^2 \quad \text{Equation 5.}$$

is a generalized series function for fitting additional parameters that are correlated to the PGNAA measurement error associated with variable belt loading. For example x could be the loading L or a function of loading L, example u could be the bulk density or a function of the bulk density, and z could be the moisture or a function of the moisture. As with Equation 4, coefficients a, b, c, d, e, f and h can be solved for using least-squares fitting of PGNAA measurement errors y to the functions x, u and z. There are no theoretical limitations to the number of terms or functions, except that there must be at least as many unique test cases of errors than the number of terms used. In such scenarios involving for example, bulk density and/or moisture, two or more unit standard sets that differ in the bulk density or moisture must be utilized to determine the measurement errors.

The powers illustrated in Equations 4 and 5 are not limited to integers and can be negative as well. The kinds of functions utilized in Equations 4 & 5 are also not limited to the examples given. Any function that accurately describes the trend of the measured error versus belt loading can be utilized.

Figure 11:
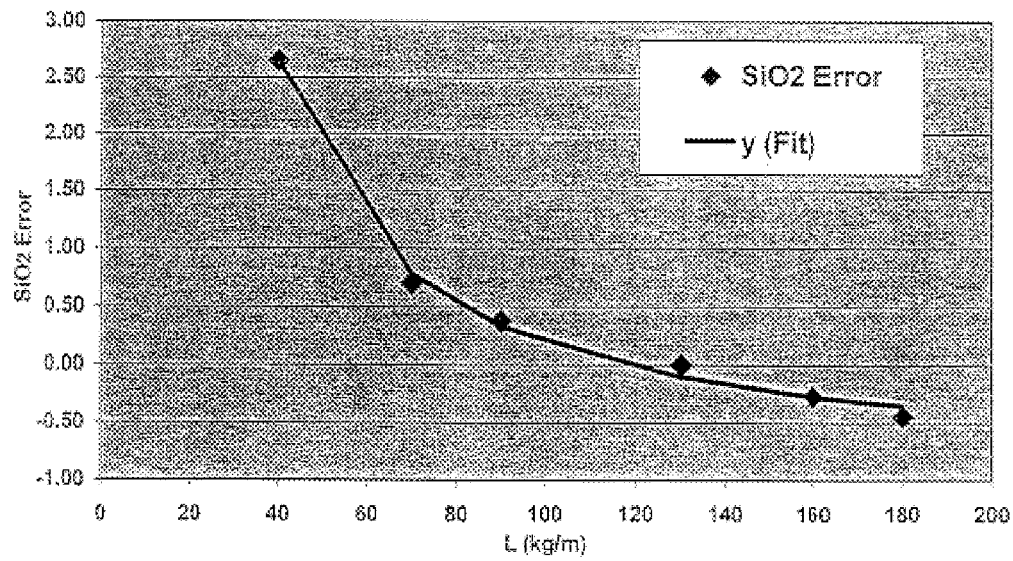
FIG. 11 is another graph of $SiO_2$ error vs. load over a range of 40 to 180 kg/m; and, FIG. 12 is a graph of CaO error vs. load over a range of 40 to 180 kg/m.

Table 3 gives the results of fitting the $SiO_2$ errors in Table 2 with a 2nd degree polynomial of Equation 4, where x=L/100. The column labeled "y(Fit)" is determined by substituting into Equation 4 the values of a, b, and c in the table, and using for x and $x^2$ also the values in the table for each test case L. FIG. 11 is plot of the $SiO_2$ error data and the y(Fit) of Table 3.

TABLE 3

Least-Squares Fit of SiO$_2$ Error to the function y = a + bx + cx$^2$ where x = L/100

| Parameter | c | b | a | F (TPH) | L (kg/m) | x | x$^2$ | SiO$_2$ Error | y (Fit) | Error of Fit |
|---|---|---|---|---|---|---|---|---|---|---|
| Coefficients | 2.2330 | −6.8809 | 4.7768 | 281 | 40 | 0.40 | 0.16 | 2.65 | 2.41 | −0.24 |
| Error Coeff | 0.7689 | 1.7352 | 0.8420 | 491 | 70 | 0.70 | 0.49 | 0.70 | 1.10 | 0.40 |
| Error of Fit | | | 0.3527 | 632 | 90 | 0.90 | 0.81 | 0.38 | 0.46 | 0.08 |
| | | | | 913 | 130 | 1.30 | 1.69 | 0.00 | −0.30 | −0.30 |
| | | | | 1123 | 160 | 1.60 | 2.56 | −0.27 | −0.40 | −0.13 |
| | | | | 1264 | 180 | 1.80 | 3.24 | −0.44 | −0.25 | 0.19 |
| | | | | | | | | | RMSD | 0.25 |

Table 4 shows the results of fitting the SiO$_2$ errors in Table 1 with x and x$^2$, where x=100/L.

TABLE 4

Least-Squares Fit of SiO$_2$ Error to function y = a + bx + cx$^2$ where x = 100/L in units of cm/kg.

| Parameter | c | b | a | F (TPH) | L (kg/m) | x | x$^2$ | SiO$_2$ Error | y (Fit) | Error of Fit |
|---|---|---|---|---|---|---|---|---|---|---|
| Coefficients | 0.2220 | 0.8598 | −0.8985 | 281 | 40 | 2.50 | 6.25 | 2.65 | 2.64 | −0.01 |
| Error Coeff | 0.1078 | 0.3351 | 0.2059 | 491 | 70 | 1.43 | 2.04 | 0.70 | 0.78 | 0.08 |
| Error of Fit | | | 0.0971 | 632 | 90 | 1.11 | 1.23 | 0.38 | 0.33 | −0.05 |
| | | | | 913 | 130 | 0.77 | 0.59 | 0.00 | −0.11 | −0.11 |
| | | | | 1123 | 160 | 0.63 | 0.39 | −0.27 | −0.27 | −0.00 |
| | | | | 1264 | 180 | 0.56 | 0.31 | −0.44 | −0.35 | 0.09 |
| | | | | | | | | | RMSD | 0.07 |

The "Error of Fit" or "Standard Error of the Estimate" is the RMSD multiplied by the square root of the number of test cases divided by the quantity of the number of test cases less the number of terms in the function y. Note that in Table 4 the Error of Fit is approximately four times less than in Table 3, indicating that x=100/L is much better than x=L/100 for this data set. Also, the RMSD value is approximately 3.5 times better for Table 4 results. FIG. 12 is plot of the SiO$_2$ error data and the y(Fit) of Table 4.

TABLE 5

Least-Squares Fit of CaO Error to function y = a + bx + cx$^2$ where x = 100/L in units of cm/kg.

| Parameter | c | b | a | F (TPH) | L (kg/m) | x | x$^2$ | CaO Error | y (Fit) | Error of Fit |
|---|---|---|---|---|---|---|---|---|---|---|
| Coefficients | −0.1530 | −1.6127 | 1.4878 | 281 | 40 | 2.50 | 6.25 | −3.49 | −3.50 | −0.01 |
| Error Coeff | 0.1994 | 0.6198 | 0.3809 | 491 | 70 | 1.43 | 2.04 | −1.26 | −1.13 | 0.13 |
| Error of Fit | | | 0.1797 | 632 | 90 | 1.11 | 1.23 | −0.27 | −0.49 | −0.22 |
| | | | | 913 | 130 | 0.77 | 0.59 | 0.00 | .16 | 0.16 |
| | | | | 1123 | 160 | 0.63 | 0.39 | 0.49 | 0.42 | −0.07 |
| | | | | 1264 | 180 | 0.56 | 0.31 | 0.53 | 0.54 | 0.01 |
| | | | | | | | | | RMSD | 0.13 |

Having derived a parametric correlation utilizing mathematical functions and parameters in the examples above, the original PGNAA instrument data in Table 1 can now be corrected at each loading or flow rate tested. For example, define the corrected value of SiO$_2$ and CaO as:

SiO$_2$(corrected)=SiO$_2$(Table 1)−y(Fit Table 4)    Equation 6.

CaO(corrected)=CaO(Table 1)−y(Fit Table 5)    Equation 7.

with results given in Table 6.

TABLE 6

Values After Compensation Using Tables 4 and 5.

| Test | L (kg/m) | F (TPH) | SiO$_2$ (corrected) | CaO (corrected) |
|---|---|---|---|---|
| 1 | 40 | 281 | 13.10 | 43.11 |
| 2 | 70 | 491 | 13.01 | 42.97 |

TABLE 6-continued

Values After Compensation Using Tables 4 and 5.

| Test | L (kg/m) | F (TPH) | SiO$_2$ (corrected) | CaO (corrected) |
|---|---|---|---|---|
| 3 | 90 | 632 | 13.14 | 43.32 |
| 4 | 130 | 913 | 13.20 | 42.94 |

TABLE 6-continued

Values After Compensation Using Tables 4 and 5.

| Test | L (kg/m) | F (TPH) | SiO$_2$ (corrected) | CaO (corrected) |
|---|---|---|---|---|
| 5 | 160 | 1123 | 13.09 | 43.17 |
| 6 | 180 | 1264 | 13.00 | 43.09 |

The results of the PGNAA accuracy enhancement versus flow rate or belt loading can determined by computing the difference between any of the corrected values and the measured value at the reference or nominal loading, which is 130 kg/m for our example. Table 7 gives the resultant relative errors of the corrected SiO$_2$(corrected) and CaO (corrected) values with respect to the original reference values of SiO$_2$ and CaO respectively in Table 1, Test 4, the reference loading or flow rate. The equations are:

$$SiO_2(corrected)Error=SiO_2(corrected)-SiO_2(Table\ 1,\ Test\ 4\ Reference),\quad \text{Equation 8.}$$

$$CaO(corrected)Error=CaO(corrected)-CaO(Table\ 1,\ Test\ 4\ Reference),\quad \text{Equation 9.}$$

Table 7 shows the errors versus loading L following correction utilizing the y fit functions for the SiO$_2$ and CaO errors.

TABLE 7

Error After Compensation (Reference = Test 4)

| Test | L (kg/m) | F (TPH) | SiO$_2$ | SiO$_2$ y (Fit) | SiO$_2$ Corr.* | SiO$_2$ Corr.* Error | CaO | CaO y (Fit) | CaO Corr.* | CaO Corr.* Error |
|---|---|---|---|---|---|---|---|---|---|---|
| 1 | 40 | 0 | 15.74 | 2.64 | 13.10 | 0.01 | 39.61 | −3.50 | 43.11 | 0.01 |
| 2 | 70 | 0 | 13.79 | 0.78 | 13.01 | −0.08 | 41.84 | −1.13 | 42.97 | −0.13 |
| 3 | 90 | 0 | 13.47 | 0.33 | 13.14 | 0.05 | 42.83 | −0.49 | 43.32 | 0.22 |
| 4* | 130 | 0 | 13.09 | −0.11 | 13.20 | 0.11 | 43.10 | 0.16 | 42.94 | −0.16 |
| 5 | 160 | 0 | 12.82 | −0.27 | 13.09 | 0.00 | 43.59 | 0.42 | 43.17 | 0.07 |
| 6 | 180 | 0 | 12.65 | −0.35 | 13.00 | −0.09 | 43.63 | 0.54 | 43.09 | −0.01 |
|  |  |  |  |  |  |  |  | RMSD | 0.07 | 0.13 |

*Corr. = corrected

The resultant RMSD vlues are reduced from 1.15 to 0.07 for SiO$_2$ (corrected) and from 1.55 to 0.13 for CaO(corrected).

The fifth step of the invention is the utilization of the real-time flow rate F (TPH) signal from a weigh scale or equivalent device to calculate expected errors for each analyzed constituent, based upon the mathematical functions, or to parameters derived in the above processes. The calculation of expected errors is done by simply substituting into Equation 4, the values of the coefficients a, b, and c determined by the least-squares or linear regression fit, and calculating the values of x and x$^2$ corresponding to the value of L determined by Equation 2, which utilizes the current real-time flow rate F. In the examples given above in Tables 3, 4 and 5, for discrete flow rates F corresponding to loadings L=40, 70, 90, 130, 160 and 180, the y(Fit) values given in the tables are the calculated expected errors.

The sixth step in the invention is applying the correction. This step corrects the PGNAA device's results by subtracting from the measurement values of an analyzed constituent the expected error associated with a specific flow rate and material loading, thereby improving the overall measurement accuracy. The corrected value C(j) on measured value of constituent j at the loading L corresponding to flow rate F using Equation 2 is defined by:

$$C(j)=M(j,L)-E(j,L) \quad \text{Equation 10.}$$

where M(j,L) is the measured value prior to correction and E(j,L) is the estimated error as a result of applying step five above for constituents j and loading L. Although the methodology of this invention was only presented two constituents, SiO$_2$ and CaO, the processes of correction described above can be utilized for any number of constituents a PGNAA device measures.

The first variant of the preferred embodiment does not require a fourth step of developing a function to predict the measurement errors, and the fifth step is different. the first, second, third, and sixth steps are the same. In this variant, the fifth step utilizes mathematical interpolation techniques such as nearest neighbor, linear, bucic, cupic spline and others for the prediction of errors of each analyzed constituent, at any given flow rate over the range of flow rates spanned by the tests, given a table of measured errors at discrete flow rates or loadings obtained from measurements such as described in the third step. As an example of simple linear interpolation, if the measured errors on SiO$_2$ were 0.70 and 0.38 at flow rates of 70 and 90 kg/m, respectively, (see Table 2), then the predicted error for SiO$_2$ at 80.0 kg/m, a flow rate midway between 70 and 90 kg/m would be mid-way between 0.70 and 0.38 which is 0.54. In this variant, the sixth step applies the estimated error to correct the measured data of the PGNAA instrument and is the same as described earlier.

The second variant of the preferred embodiment does not require a fourth step of developing a function to predict the measurement errors, and the fifth step is different. The first, second, third, and sixth steps are the same. In this variant, the fifth step utilizes rule-based assignment of a previously measured error at a discrete flow rate or loading L that most closely matches the current flow rate or loading. One example is the rule of closest proximity where the estimated error is taken from that specific line or record of a table of measured errors where the loading value in the table is most closely the current or real-time loading value of material flowing through the PGNAA instrument. Thus, if the measured errors on CaO were −1.26 and −0.27 at flow rates of 70 and 90 kg/m respectively (see Table 2), then the predicted error for CaO at 75 kg/m, a flow rate closest 70 kg/m in the table is −1.26. This approach works well when the table of measured errors contains many rows or records, each measured at small increments of flow rate, such as 70, 72, 74, 76 . . . kg/m. In this variant, the sixth step applies the estimated error to correct the measured data of the PGNAA instrument and is the same as described earlier.

In another variant of the preferred embodiment, two or more set of unit standards having a different chemistry are utilized. The process steps of (a) providing the unit standards, (b) arranging profiles of standard units for measurement, (c) successively measuring each profile and tabulating the results to obtain observed differences or errors, (d) mathematically fitting the measured errors to a mathematical expression are the same as described in the preferred embodiment, (e) steps (a–d) are repeated for each of the unit standard sets of different chemistries, maintaining the association of each set of fitted parameters to the specific chemistry of the set of unit standards yielding the data, (f) determining which specific set of unit standards matches most closely the current real-time PGNAA measured chemistry, and selecting the specific set of mathematically fitted parameters associated with that specific set of unit standards, (g) utilizing the real-time flow rate of the unknown material to calculate expected errors for each constituent based upon the mathematical functions and parameters derived in the previous steps; and (h) subtracting the estimated or predicted measurement errors determined in the prior steps from the measured values to determine the corrected or true value. Utilizing more than one chemistry set generally produces more accurate correction of PGNAA analysis values because the chemistry itself influences the magnitude of the neutron flux in the analyzer and the gamma ray attenuation therefore influences the magnitude of the background signals that contribute to the measurement errors at different loadings.

In another variant of the preferred embodiment, two or more set of unit standards having a different chemistry are utilized. The process steps of (a) providing the unit standards, (b) arranging profiles of standard units for measurement, (c) successively measuring each profile and tabulating the results to obtain observed differences or errors, (d) steps (a–c) are repeated for each of the unit standard sets of different chemistries, maintaining the association of each set of fitted parameters to the specific chemistry of the set of unit standards yielding the data, (e) determining which specific set of unit standards matches most closely the current real-time PGNAA measured chemistry, and selecting the specific set of mathematically fitted parameters associated with that specific set of unit standards, (f) determining the expected errors for each constituent at the current real-time flow rate by using techniques of mathematical interpolation of the data set determined in steps c) and e) to derive the best estimates of the measurement error by using error values from testing at both higher and lower belt loadings than the current real-time flow rate; and (g) subtracting the estimated or predicted measurement errors determined in the prior step to determine the corrected or true value.

In another variant of the preferred embodiment, two or more sets of unit standards having a different chemistry are utilized. The process steps are (a) providing the unit standards, (b) arranging profiles of standard units for measurement, (c) successively measuring each profile and tabulating the results to obtain observed differences or errors, (d) steps (a–c) are repeated for each of the unit standard sets of different chemistries, maintaining the association of each set of fitted parameters to the specific chemistry of the set of unit standards yielding the data, (e) determining which specific set of unit standards matches most closely the current real-time PGNAA measured chemistry, and selecting the specific set of mathematically fitted parameters associated with that specific set of unit standards, (f) determining the expected errors for each constituent at the current real-time flow rate by rule-base or proximity selection of the measured error value from a table of previously measured errors determined in steps (c and e), where the location of the error in the table to be used is that location associated with a loading or flow rate value that most closely matchers the current real-time flow rate; and (g) subtracting the estimated or predicted measurement errors determined in the prior step to determine the corrected or true value.

In another variant of the preferred embodiment, two or more sets of unit standards having a different chemistry are utilized for the purposes of generating loading specific calibration parameter sets. In prior art, PGNAA instruments are normally calibrated at only one loading, that is representative of the average flow rate during use. By using two or more sets of unit standards, each having a different chemistry, one calibration parameter set can be generated for each measured constituent for each of several different loadings spanning the loading range over which the instrument will be used. A loading specific calibration parameter set is especially accurate when the amount of material flowing through the PGNAA device matches or falls within a limited range above and below the amount of load used for in the specific calibration. A calibration parameter set involves a mathematical function, algorithm or association that, when applied to the unadjusted output data of a measuring instrument, will yield a result that equals or closely matches the known value of the calibration standard that the instrument is measuring. Linear Regression is one common method for generating a calibration parameter set. The process steps are (a) providing two or more sets of chemistries, in the form of standard geometric units, each unit having the same concentration of the specific constituent to be measured and in the form that can be arranged to pass through the analyzer in the same manner as the bulk material, (b) arranging the units for insertion into the analyzer in geometries and quantities referred to as "loading profiles" that range from the smallest to the largest flow rates to be expected with the specific bulk material and the specific analyzer, (c) from the selected loading profiles determined above, choosing one profile and successively inserting different chemistry sets into the analyzer and measuring long enough to yield a measurement uncertainty that is small compared to re-measurement, and recording these results in a table of calibration data with an associated loading, (d) repeating steps (b–c) are for each loading profile determined in step (b); (e) calibrating the PGNAA device separately for each constituent and each loading profile and storing the loading specific sets of calibration parameters for each measured constituent in a data table accessible by the PHNAA device; (f) determining by utilizing the current real-time loading signal, which loading specific set of calibration parameters determined and stored in step (e) is the closest match to the loading profile measured in step (c), and selecting that calibration parameter set for the analyzer's measurement of unknown materials; (g) applying the loading specific calibration set determined in step (f) to the PGNAA device in order that the real-time measured values are high in accuracy.

In another variant of the method described above, having generated two or more loading specific calibration parameter sets for each constituent, the optimal calibration parameter set at a given current loading, that does not exactly match any of the loadings utilized when the instrument was calibrated, can be mathematically generated by interpolation. For example, if calibration parameter sets are generated only for loadings of 50 and 100 kg/m, and the instrument is measuring an unknown material at a current flow equivalent to 70 kg/m, then the technique of mathematical interpolation can be used to generate a set of calibration parameters for the 70 kg/m loading. In a simple example of linear interpolation, if for one constituent a particular calibration parameter was 1.05 for the 50 kg/m case and 1.10 for the 100 kg/m case, then that calibration parameter for 70 kg/m would be 1.07. This method provides a higher accuracy result than simply using the 50 kg/m calibration parameter set or the 100 kg/m calibration parameter set.

In another variant applicable to all methods described above, specific amounts of homogenized and standardized bulk material, contained or un-contained, may be utilized in place of a specific number of unit standards to provide a specific loading. The term "standardized" used here means the chemistry is well-known. The processes described above are not limited to utilization of unit standards, although utilizing of unit standards has many advantages in ease of loading profile creation and ease of insertion into the PGNAA instrument.

The methods for error prediction and measured value correction are not limited to the examples given above. There are many variants. For a given application, the optimal method for best accuracy may require testing, comparison and evaluation of several methods.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the same way to achieve substantially the same result are within the scope of this invention.

What is claimed is:

1. A method of maintaining measurement accuracy of specific constituents in prompt gamma neutron activation analyzers in a flow of bulk material having a known range of flow rates comprising of the steps of:

(a) providing a plurality of samples of the bulk material in the form of standard geometric units, each said unit having the same concentration of the specific constituent to be measured and arranging said units in a form that can pass through the analyzer in the same manner as the bulk material; for insertion into the analyzer in geometries and quantities referred to as "loading profiles" that range from the smallest to the largest flow rates to be expected with the specific bulk material and the specific analyzer;

(b) successively inserting each of the loading profiles into the analyzer and measuring long enough to yield a measurement uncertainty that is small compared to the observed differences in analysis results from one loading to another, and recording these results and computing the differences of the measurements between loading profiles, hereafter referred as measured errors, in a table, and then removing the loaded profiles;

(c) mathematically fitting the measured errors for each constituent at each loading to one or more mathematical expressions that are derived from the loading values, so as to allow subsequent mathematical generation of the expected error at any loading value;

(d) utilizing the real-time flow rate of the unknown material to calculate expected errors for each constituent based upon the mathematical functions and parameters derived in said previous steps; and, (e) subtracting the estimated or predicted measurement errors determined in the prior step from the measured values to determine the corrected or true value.

2. The method claim 1 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

3. A method of maintaining measurement accuracy of specific constituents in prompt gamma neutron activation analyzers in a flow of bulk material having a known range of flow rates comprising the steps of:

(a) providing a plurality of samples of the bulk material in the form of standard geometric units, each said unit having the same concentration of the specific constituent to be measured and arranging said units in a form that can pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) successively inserting each of the loading profiles into the analyzer and measuring long enough to yield a measurement uncertainty that is small compared to the observed differences in analysis results from one loading to another, and recording these results and computing the differences of the measurements between loading profiles, hereafter referred as measured errors, in a table, and then removing the loaded profiles;

(d) determining the expected errors for each constituent at the current real-time flow rate of the unknown material by using techniques of mathematical interpolation to derive the best estimates of the measurement error by using error values from testing at both higher and lower belt loadings than the current real-time flow rate; and, (e) subtracting the estimated or predicted measurement errors determined in the prior step from the measured values to determine the corrected or true value.

4. The method claim 3 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

5. A method of maintaining measurement accuracy of specific constituents in prompt gamma neutron activation analyzers in a flow of bulk material having a known range of flow rates comprising the steps of:

(a) providing a plurality of samples of the bulk material in the form of standard geometric units, each said unit having the same concentration of the specific constituent to be measured and said units in a form that can be arranged to pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) successively inserting loading profiles into the analyzer and measuring long enough to yield a measurement uncertainty that is small compared to the observed differences in analysis results from one loading to another, and recording these results and computing the differences of the measurements between loading profiles, hereafter referred as measured errors in a table, and then removing the loaded profiles;

(d) determining the expected errors for each constituent at the current real-time flow rate by rule-base or proximity selection of the measured error value from a table of previously measured errors, where the location of the error in the table to be used is that location associated with a loading or flow rate value that most closely matches the current real-time flow rate or loading of the unknown material;

(e) subtracting the estimated or predicted measurement errors determined in the prior step from the measured values to determine the corrected or true value.

6. The method claim 5 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

7. A method of maintaining measurement accuracy of specific constituents in prompt gamma neutron activation analyzers in a flow of bulk material having a known range of the flow rates comprising the steps of:

(a) providing a plurality of samples of the bulk material in the form of standard geometric units, each said unit having the same concentration of the specific constituent to be measured and said units in a form that can be arranged to pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) successively inserting each of the loading profiles into the analyzer and measuring long enough to yield a measurement uncertainty that is small compared to the observed differences in analysis results from one loading to another, and recording these results and computing the differences of the measurements between loading profiles, hereafter referred as measured errors, in a table, and then removing the loaded profiles;

(d) mathematically fitting the measured errors for each constituent at each loading to one or more mathematical expressions that are derived from the loading values, so as to allow subsequent mathematical generation of the expected error at any loading value;

(e) repeating steps (a–d) for at least one more set of unit standards having different chemistry than the first set of unit standards, maintaining the association of each set of fitted parameters to the specific chemistry of the set of unit standards yielding the data;

(f) determining which specific set of unit standards matches most closely the current real-time PGNAA measured chemistry, and selecting the specific set of mathematically fitted parameters associated with that specific set of unit standards;

(g) utilizing the real-time flow rate of the unknown material to calculate expected errors for each constituent based upon the mathematical functions and parameters derived in said previous steps; and, (h) subtracting the estimated or predicted measurement errors determined in the prior steps from the measured values to determine the corrected or true value.

8. The method claim 7 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

9. A method of maintaining measurement accuracy of specific constituents in prompt gamma neutron activation analyzers in a flow of bulk material having a known range of flow rates comprising the steps of:

(a) providing a plurality of samples of the bulk material in the form of standard geometric units, each said unit having the same concentration of the specific constituent to be measured and said units in a form that can be arranged to pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) successively inserting each of the loading profiles into the analyzer and measuring long enough to yield a measurement uncertainty that is small compared to the observed differences in analysis results from one loading to another, and recording these results and computing the differences of the measurements between loading profiles, hereafter referred as measured errors, in a table, and then removing the loaded profiles;

(d) repeating step (c) with at least one more set of unit standards having a different chemistry;

(e) determining which specific set of unit standards matches most closely the current real-time PGNAA measured chemistry, and selecting the specific set of measured data from step (c) for input to the next step;

(f) determining the expected errors for each constituent at the current real-time flow rate by using techniques of mathematical interpolation of the data set determined in steps (c) and (e) to derive the best estimates of the measurement error by using error values from testing both at higher and lower belt loadings than the current real-time flow rate;

(g) subtracting the estimated or predicted measurement errors determined in the prior step to determine the corrected or true value.

10. The method claim 9 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

11. A method of maintaining measurement accuracy of specific constituents in prompt gamma neutron activation analyzers in a flow of bulk material having a known range of flow rates comprising the steps of:

(a) providing a plurality of samples of the bulk material in the form of standard geometric units, each said unit having the same concentration of the specific constituent to be measured and said units in a form that can be arranged to pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) successively inserting each of the loading profiles into the analyzer and measuring long enough to yield a measurement uncertainty that is small compared to the observed differences in analysis results from one loading to another, and recording these results and computing the differences of the measurements between loading profiles, hereafter referred as measured errors, in a table, and then removing the loaded profiles;

(d) repeating step (c) with at least one more set of unit standards having a different chemistry;

(e) determining which specific set of unit standards matches most closely the current real-time PGNAA measured chemistry, and selecting the specific set of measured data from step (c) for input to the next step;

(f) determining the expected errors for each constituent at the current real-time flow rate by rule-base or proximity selection of the measured error value from a table of previously measured errors determined in steps (c) and (e), where the location of the error in the table to be used is that location associated with a loading or flow rate value that most closely matches the current real-time flow rate or loading;

(g) subtracting the estimated or predicted measurement errors determined in the prior step from the measured values to determine the corrected or true value.

12. The method claim 11 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

13. A method of maintaining measurement accuracy of specific constituents in prompt gamma neutron activation analyzers in a flow of bulk material having a known range of flow rates comprising the steps of:

(a) providing two or more sets of chemistries, each set comprised of a plurality of samples of the bulk material in the form of standard geometric units, each said unit having the same concentration of the specific constituent to be measured and said units in a form that can be arranged to pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) from the selected loading profiles determined above, choose one profile and successively insert different chemistry sets into the analyzer and measuring long enough to yield a measurement uncertainty that is small compared to re-measurement, and recording these results in a table of calibration data with an associated loading;

(d) repeating steps (b) and (c) for each loading profile determined in step (a);

(e) calibrating the PGNAA device separately for each constituent and each loading profile and storing the loading specific sets of calibration parameters for each measured constituent in a data table accessible by the PGNAA device;

(f) determining by utilizing the current real-time loading signal, which loading specific set of calibration parameters determined and stored in step (e) is the closest match to the loading profile measured in step (c) and selecting that calibration parameter set for the analyzer's measurement of unknown materials in current time;

(g) applying that loading specific calibration set determined in step (f) to the PGNAA device in order that the real-time measured values are high in accuracy.

14. The method claim 13 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

15. A method of maintaining measurement accuracy of specific constituents in prompt gamma neutron activation analyzers in a flow of bulk material having a known range of flow rates comprising the steps of:

(a) providing two or more sets of chemistries, each set comprised of a plurality of samples of the bulk material in the form of standard geometric units, each said unit having the same concentration of the specific constituent to be measured and said units in a form that can be arranged to pass through the analyzer in the same manner as the bulk material;

(b) arranging said units for insertion into the analyzer in geometries and quantities referred to as loading profiles that range from the smallest to the largest flow rates to be expected with the specific bulk material and the specific analyzer;

(c) successively insert different chemistry sets into the analyzer and measuring long enough to yield a measurement uncertainty that is small compared to re-measurement, and recording these results in a table of calibration data with an associated loading;

(d) repeating steps (b) and (c) for each loading profile determined in step (a);

(e) calibrating the PGNAA device separately for each constituent and each loading profile and storing the loading specific sets of calibration parameters for each measured constituent in a data table accessible by the PGNAA device;

(f) determining by utilizing the current real-time loading signal, which two loading specific sets of calibration parameters determined and stored in step (e) bracket the current loading profile;

(g) utilizing the current real-time loading signal, generate a set of calibration parameters for each measured constituent that is optimal for the current loading, by mathematical interpolation on the two loading specific calibration parameter sets that bracket the current loading;

(h) applying that loading specific calibration set determined by interpolation to the PGNAA device in order that the real-time measured values are high in accuracy.

16. The method claim 15 of maintaining measurement accuracy of specific constituents in prompt gamma neutron activation analyzers in a flow of bulk material having a known range of flow rates, wherein specific amounts of homogenized and standardized bulk material, contained or uncontained is utilized in place of a specific number of unit standards to provide a specific loading.

* * * * *